United States Patent [19]
Pannozzo

[11] Patent Number: 5,582,189
[45] Date of Patent: Dec. 10, 1996

[54] METHOD FOR DIAGNOSING THE SUBLUXATION OF A SKELETAL ARTICULATION

[76] Inventor: Anthony N. Pannozzo, 3755 Barber Dr., Canfield, Ohio 44406

[21] Appl. No.: 327,559

[22] Filed: Oct. 24, 1994

[51] Int. Cl.$^6$ ............................. H05G 1/28; A61B 6/08
[52] U.S. Cl. .................................................. 128/898
[58] Field of Search ............................ 128/897, 898, 128/630, 653.1; 482/902; 364/413.02, 413.03, 413.22; 378/162–164, 205; 250/491.1

[56] References Cited

U.S. PATENT DOCUMENTS

| | | | |
|---|---|---|---|
| 3,171,959 | 8/1962 | Kozek et al. | 378/164 |
| 4,479,498 | 10/1984 | Toftness | 128/653.1 |
| 5,052,035 | 9/1991 | Krupnick | 378/164 |
| 5,239,569 | 8/1993 | Saleh et al. | 378/163 |

Primary Examiner—Angela D. Sykes
Assistant Examiner—Samuel Gilbert
Attorney, Agent, or Firm—Mueller and Smith, LPA

[57] ABSTRACT

A method for diagnosing in a human body a subluxation of an articulation from its normal anatomical alignment. An imagable surface is aligned generally parallel to a pair of coordinate axes which correspond to the normal anatomical alignment of the articulation. The articulation is disposed in a known position with respect to the coordinate axes, and is imaged on the imagable surface to expose the subluxed axis thereof. The image of the articulation is aligned with indicia corresponding to the coordinate axes to dispose the image in the known position with respect to indicia. The degree of subluxation of the articulation from its normal anatomical alignment then may be determined by measuring the deviation of the subluxed axis from the indicia.

21 Claims, 4 Drawing Sheets

METHOD FOR DIAGNOSING THE SUBLUXATION OF A SKELETAL ARTICULATION

BACKGROUND OF THE INVENTION

The present invention is directed to a method for diagnosing the subluxation of a skeletal articulation which may be an appendicular joint or an intervertebral joint of the spinal column.

It has been reported that 60% to 80% of the general population will experience at least one episode of low back pain (LBP). Fischgrund, J. S., and Montgomery, D. M., "Diagnosis and Treatment of Discogenic Low Back Pain," Orthopaedic Review, 22(3), pp. 311–318 (March 1993) [1]. Indeed, at any given time, more than 10% of the population is reported to suffer some degree of LBP. Katz, J. N. "The Assessment and Management of Low Back Pain: A Critical Review." Arthritis Care and Research, 6(2), pp. 104–14 (June 1993) [2]. The direct medical costs associated with the treatment of LBP in 1990 were estimated to have exceeded $23 billion in the United States alone[2]. Indirect costs, including the lost wages of injured workers, the lost earnings of spouses who cared for injured spouses, and production losses to employers, additionally range from between $10 and $20 billion annually [2].

The diagnosis and treatment of LBP may be analogized to an engineering problem. In structure, as described by Gray, "Anatomy, Descriptive and Surgical," Bounty Books, N.Y. (1997) [3], and by Williams, P. L., Warick, R., Dyson, M., and Bannister, L. H., "Gray's Anatomy," 37th ed., Churchill Livingstone, Edinburgh (1989) [4], the spine is a flexible column of bone formed from the junction of the vertebrae. The vertebrae generally are thirty-three in number, and are designated according to position along the column as seven cervical (C1–7), twelve thoracic (T1–12), five lumbar (L1–L5), five sacral (S1–S5), and four coccygeal (Co1–Co4). According to the general vertebrate plan, the spine is situated dorsally in the median line of the human body. Viewed anteriorly, the spine presents two pyramidal regions, an upper formed of the vertebrae from C2 through L5, and a lower formed of the sacrum and the coccyx. The upper region increases in mass and width from an apex at the first cervical vertebra or atlas through L5, which increase is indicative of a corresponding increase in load bearing capacity. The increased load bearing capacity is paralleled by decreased flexibility, making the lumbar region more prone to injury and accompanying LBP.

Viewed laterally, the spinal column presents several curves corresponding to the different vertebral regions. The cervical curve, which is the least marked, is convex forward from the atlas to T2. The thoracic curve is concave forward and reaches from T2 to T12. The lumbar curve which, like the cervical, is convex forward extends from T12 to L5. The spine additionally may present a slight lateral curve in the upper thoracic region. This laterally curve is generally convex to the right in right-handed persons, and convex to the left in left-handed persons.

Each vertebra consists of a ventral body which is solid, and a dorsal arch formed of two pedicles, two laminae, and seven lever-like processes, viz., four articular, two transverse, and one spinous. The transverse and spinous processes of the vertebrae serve as levers for the attachment of the muscles which articulate the spine. Together, the processes enclose a vertebral foramen which is occupied by the spinal cord, meninges, and their vessels. Opposing surfaces of adjacent bodies are bound together in a stack by intervertebral discs of fibrocartilage. In such an arrangement, the bodies of the vertebrae form a column-like structure for supporting the cranium and trunk, with the vertebral foramina forming an annular vertebral canal posterior of the bodies for receiving and protecting the spinal cord. Between adjoining arches, near their junctions with the bodies, are formed intervertebral foramina which transmit spinal nerves, smaller recurrent nerves, and blood and lymphatic vessels. The complete column of bodies and discs forms a strong but flexible central axis of the body. The column itself supports the full weight of the head and trunk, and, with the attached muscles, transmits even greater forces.

Although movement between adjacent vertebrae is limited to small ranges of motion, the summation of these ranges gives considerable degrees of bending freedom in flexion, extension, lateral flexion, rotation, and circumduction. The principal sites of movement between the vertebrae is found at the intervertebral discs. The elastic deformability of the discs facilitates tilting and torsion between the vertebral bodies, and additionally gives the column a degree of compressibility which allows the spines, with its curvatures, to better dampen stresses from the thrusts of the feet during walking, running, or jumping. Although the discs play a prominent role in spinal dynamics, regional variations in mobility also are affected by the disposition, properties, and geometries of intervertebral synovial joints and ligamentous complexes attached to the vertebrae.

Clinically, LBP generally is categorized as mechanical, which is centered in the lower lumbar region, sciatic, which radiates down the left in the distribution of the sciatic nerve, and stenosis, involving a compression of the caudal equina and an associated polyradicular pain pattern exacerbated with lumbar extension [2]. LBP often presents simply as a manifestation of strains and sprains of the spinal facet joints and soft tissues of the lower back area. Chilton, M. D., and Nisenfeld, F. G., "Nonoperative Treatment of Low Back Injuries in Athletes," Clinics in Sports Medicine, 12(3), pp. 547–55 (July 1993) [5]. Skeletal and discogenic causes, although somewhat less common, also are contributory and include spinal fractures, disorders of the vertebral discs such as herniations and spinal stenosis, and vertebral subluxations such as ithmic spondylolisthesis, spinal ostechondrosis, scoliosis, hyperlordosis, kyphosis, and other misalignments [1,2,5]. Vertebral subluxations, which result from the abnormal movement of subluxed vertebrae in response to applied physiologic loads, are known to particularly affect the spinal cord and its associated nerves through pressure or other interference or irritation mechanisms.

Heretofore, only 10% of 20% of patients with acute or chronic LBP could be given a definitive pathoanatomic diagnosis [5]. Indeed, it has been reported that only 2% of routine films taken in connection with the initial evaluation of patients complaining of LBP showed any significant radiographic findings [5]. More sophisticated and expensive imaging techniques, such as computed tomography (CT), magnetic resonance imaging (MRI), or myelography, therefore are often specified as part of the examination protocol, and heretofore have been believed required to make definitive diagnoses of herniated discs, spinal stenosis, and most tumors and infections [2]. Diagnoses made with even the more sophisticated imaging techniques such as MRI, however, do not always correlate with LBP [1]. Radiographs therefore continue to be frequently employed in the evaluation of patients with LBP [2]. In this regard, it has been suggested that imaging studies should not be used to make a diagnosis, for example, of herniated disc, spinal stenosis, or other pain syndromes, but rather to confirm diagnoses made on the basis of patient history and physical examination [2].

The pathology associated with a clinical diagnosis of LBP heretofore has been confirmed solely on the basis of the visual observation of anterior, posterior, or profile images of the spine. Objective assessment of subluxations, however, has proven difficult as resulting from deformations, pressure fractures, depressed fractures, and the like which require the measuring of individual differences. Accordingly, systems have been proposed for measuring spinal misalignments, deformations, and instabilities. For example, Benesh et al., U.S. Pat. No. 5,088,504, describe a device for measuring skeletal misalignments which involves determining the lateral weight distribution in a patient, which weight distribution may then be related to the skeletal distortion.

Brown et al., U.S. Pat. No. 4,899,761, describe an apparatus for measuring the instability of a motion segment of the spine. The device has a vertebrae distractor which includes a means for applying a constant rate of increasing force against adjacent vertebrae of the motion segment to separate the vertebrae, and a means for recording the changes in the resistance of the vertebrae to the separation. The data obtained then are compared to results obtained from motion segment units in unfixed cadaveric spines or to the subjective testing of the patient using a Kocher clamp.

Yamashita et al., European Patent Application 0 245 098, describe a method for judging the deformation of a vertebral body. The method involves measuring a central, front brim, and rear brim length from a digitized profile X-ray image of the vertebral body, and then determining ratios derived from such lengths to classify the body.

Although the above-described systems may be said to represent an advancement in the art of LBP assessment, such systems have yet to be universally accepted by practitioners as being either prohibitively costly or in lacking documented clinical benefits. Without an accepted methodology for localizing the source of LBP, the nonsurgical treatment thereof has focused on nonspecific modalities such as bed rest, administration of nonsteroidal, anti-inflammatory drugs, muscle relaxants, or narcotics, exercise, or chiropractic manipulation [2,5]. The failure of such generalized modalities, however, frequently leads to surgical treatments, but often without any clearly beneficial results [1].

In view of the uncertain prognosis of the generalized treatment modalities, there have been calls for improved methods of localizing the exact sources of LBP. Waddell, G., "A New Clinical Model for the Treatment of Low-Back Pain," Spine, 12(7), pp. 634–642 (1987) [6]. The preferred method would be part of a comprehensive and cost-effective management protocol for diagnosing and treating a patient presenting a LBP or the like, and would be adaptable for diagnosing subluxations of both intervertebral and appendicular articulations. It is apparent that such a method would be well-received by practitioners, and would represent an important improvement in physiatrics.

BROAD STATEMENT OF THE INVENTION

The present invention is addressed to a method for diagnosing the subluxation of an articulation, such as an appendicular joint or an intervertebral joint of the spinal column, having a skeletal structure normally in an anatomical alignment. In providing for the alignment of an image of the subluxed axis of the articulation with a pair of coordinate axes corresponding to the normal anatomical alignment of the articulation, the method allows for an objective determination of the degree of subluxation through the measurement of the deviation of the subluxed axis of the articulation from indicia corresponding to the coordinate axes. Such objective determination assists the practitioner in rendering a more definitive pathogenic diagnosis of the physiological cause of the LBP or the like, as well as in confirming diagnoses made on the basis of patient history and physical examination.

It therefore is a feature of the invention to provide a method for diagnosing in a patient a subluxation of an articulation from its normal anatomical alignment. An imagable surface is aligned generally parallel to a pair of coordinate axes which correspond to the normal anatomical alignment of the articulation. The articulation is disposed in a known position with respect to the coordinate axes, and is imaged on the imagable surface to expose the subluxed axis thereof. The image of the articulation is aligned with indicia corresponding to the coordinate axes to dispose the image in the known position with respect to the indicia. The degree of subluxation of the articulation from its normal anatomical alignment then may be determined by measuring the deviation of the subluxed axis from the indicia.

In a preferred embodiment, the method of the invention is part of a comprehensive management protocol for the diagnosing and treating of a patient experiencing pain in the range of motion of an articulation. Within such a protocol, the method may be used to assist the practitioner in localizing the physiological cause of the LBP or like symptomology. With the source of pain localized, a treatment modality, which preferably is nonoperative, may be prescribed which is specific to that source rather than generalized. Such a treatment modality clinically has been observed to effect a more favorable prognosis than the generalized methods heretofore recommended in the literature.

The invention, accordingly, comprises the method possessing the arrangement of steps which is exemplified in the following detailed description. Reference to that description and to the accompanying drawings should be had for a fuller understanding and appreciation of the nature and objects of the invention, although other objects may be obvious to those skilled in the art.

BRIEF DESCRIPTION OF THE DRAWINGS

For a fuller understanding of the nature and objects of the invention, reference should be had to the following detailed description taken in connection with the accompanying drawings wherein.

The drawings will be described further in connection with the following Detailed Description of the Invention.

DETAILED DESCRIPTION OF THE INVENTION

The present invention is addressed to a method for diagnosing the subluxation of an articulation, which may be appendicular joint or an intervertebral joint of the spinal column, having a skeletal structure normally in an anatomical alignment. In this regard, an imagable surface is aligned generally parallel to a pair of coordinate axes which correspond to the normal anatomical alignment of the articulation. The articulation is disposed in a known position with respect to the coordinate axes, and is imaged on the imagable surface to expose the subluxed axis thereof. The image of the articulation is aligned with indicia corresponding to the coordinate axes to dispose the image in the same known position with respect to the indicia as the articulation was disposed with respect to indicia. The degree of subluxation of the articulation from its normal anatomical alignment then may be determined by measuring the deviation of the subluxed axis from the indicia.

Figure 1:
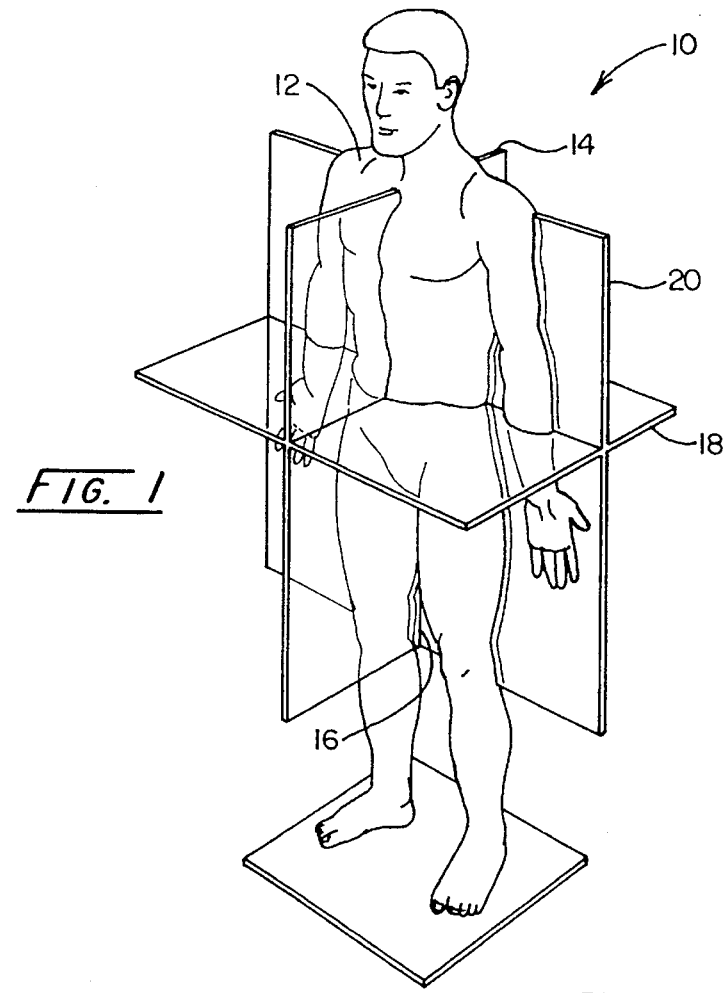
FIG. 1 is an anterior perspective view of an anatomic, palms forward positioning of a human body showing the intersections of a sagittal, a transverse, and a coronal reference plane therethrough.

Referring then to the figures wherein the above-described method of the invention is detailed, shown generally at 10 in FIG. 1 is a typical anatomic, palms forward positioning of a human body, 12. As is presented by Jacob, S., and Francone, C., "Structure and Function of Man," 3d ed., W. B. Saunders Co., Philadelphia, Penn. (1974), body 12 may be described by convention with respect to a set of orthogonal reference planes. In particular, a mid-sagittal plane, 14, is shown as vertically dividing body 12 through a midline, 16, into right and left portions. Similarly, a mid-transverse plane, 18, is shown as dividing body 12 into superior and inferior portions, with a coronal plane, 20, shown as dividing body 12 into anterior and posterior portions. It will be appreciated that other sagittal, transverse, and coronal planes may be referenced by translating each of planes 14, 18, or 20 with respect to midline 16. From the intersections of the sagittal, transverse, and coronal planes, any number of coordinated axes may be defined which correspond to the normal anatomical alignment of the articulations, such as the intervertebral and appendicular joints, of body 12.

Figure 2:
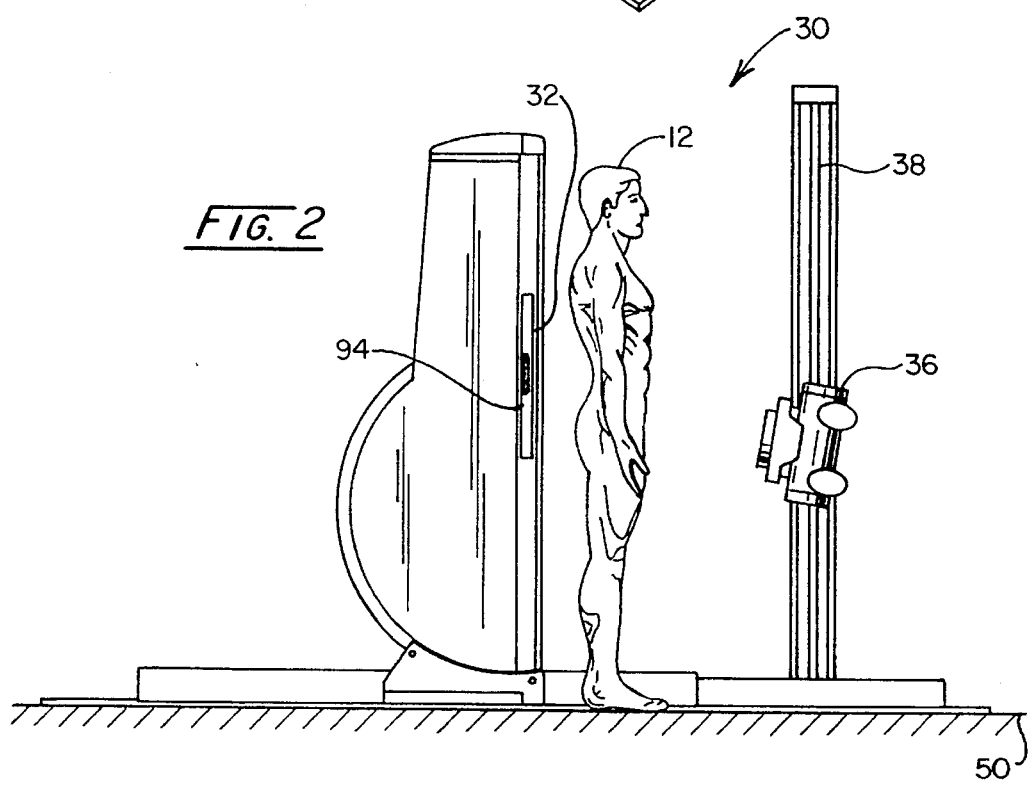
FIG. 2 is a lateral view of an arrangement for imaging a subluxed articulation of a patient which apparatus, in accordance with the precepts of the present invention, is provided has having an imagable surface aligned generally parallel to a pair of coordinate axes corresponding to the normal anatomical alignment of the articulation.

With the normal anatomical alignment of the articulations of body 12 thus defined, the discussion may proceed to a consideration of the methodology of the present invention. Looking then FIG. 2, shown generally at 30 is an arrangement in accordance with the invention for imaging a subluxation of an articulation of body 12. Arrangement 30 may be seen to comprise an imagable surface, 32, which may be an unexposed radiographic film. Surface 32 is supported by a housing, 34, for movement along a longitudinal axis thereof, and is spaced a predetermined distance from a fluoroscope, 36, or the like. Fluoroscope 36, in turn, is supported by a tower, 38, also for movement along a longitudinal axis thereof in accordance with the movement of surface 32. As may be appreciated with additional reference to FIG. 3, imagable surface 32 is aligned generally parallel to a pair of coordinate axes, 40a and 40b, which axes correspond to the normal anatomical alignment, as was described in connection with FIG. 1, of the articulation of interest.

For imaging the articulation to expose the subluxed axis thereof, body 12 is positioned before imagable surface 32 intermediate fluoroscope 36 such that the articulation thereof is disposed in a known position with respect to coordinate axes 40. In this regard, it is preferred that an intersection of an orthogonal pair of the sagittal, coronal, and transverse planes (FIG. 1) referencing body 12 are aligned with coordinate axes 40. For example, for the imaging of an intervertebral joint of the spinal column, body 12 may be disposed such that the intersection of mid-sagittal plane 14 and mid-transverse plane 18 are aligned with axes 40. Similarly, for the imaging of an appendicular joint such as the genu or carpus, the intersection of the corresponding sagittal and transverse planes may be aligned with axes 40. Such alignments may be achieved, for example, by disposing surface 32 generally perpendicular to a support surface, 50, upon which body 12 may be received in a manner wherein the intersections of the reference planes thereof are in correspondence with axes 40.

Figure 3:
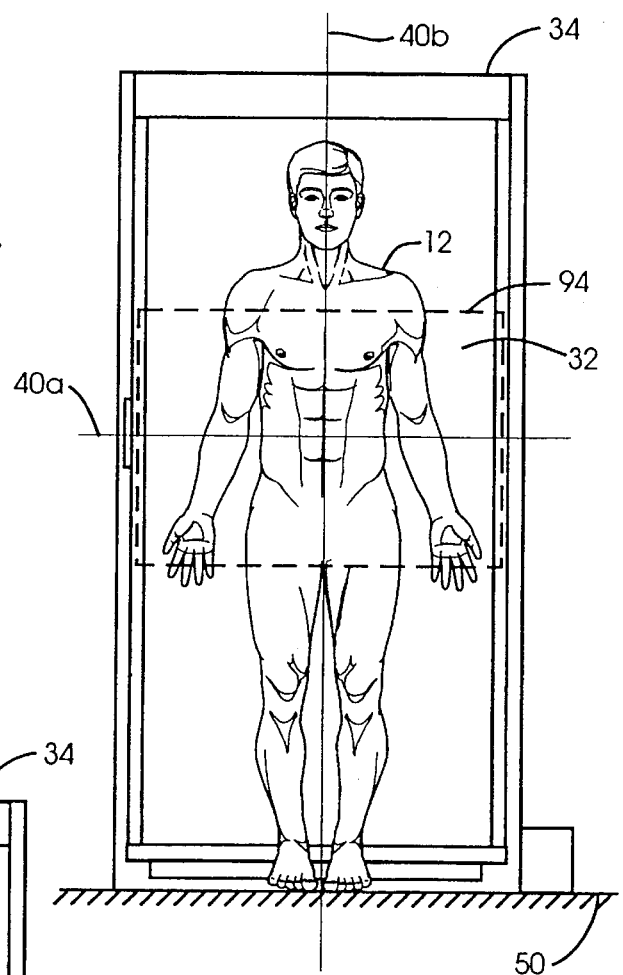
FIG. 3 is an anterior view showing the patient of FIG. 2 as disposed in a known position with respect to the coordinate axes for the imaging of the subluxed articulation to expose the subluxed axis thereof.

As is shown in FIGS. 2 and 3, for the imaging of an intervertebral joint, a carpus, or a like load-bearing articulation, it is preferred that a normal physiologic load be applied prior to the imaging of the articulation by, for example, disposing body 12 in a standing position on support surface 50. In this way, the relationship of the constituent parts of the articulation may be examined to reveal any subluxations which, when under load, are the source of pain inuring in the range of motion.

With the articulation of body 12 aligned in a known position with respect to coordinate axes 40, imagable surface 32 may be radiographically or otherwise exposed to reveal the subluxed axis of the articulation in either an anterior, posterior, or lateral view. As may be seen in FIG. 6 at 32b for a posterior view of a subluxed spinal column, 52', and, for purposes of comparison, in FIG. 4 at 32a for a posterior view of a normal spinal column, 52, exposed surface 32 reveals the morphology of the articulation of interest. For illustrative purposes, exposures 32a and 32b are shown as positive rather than as negative images.

Figure 4:
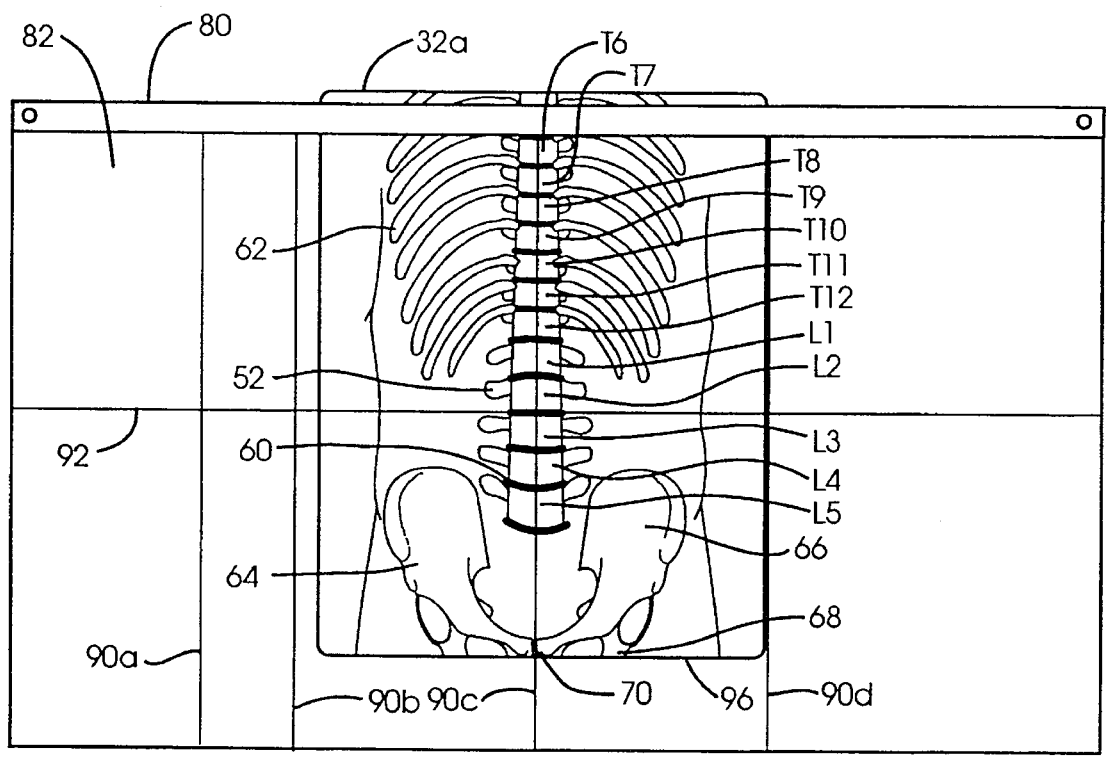
FIG. 4 is a stylized, graphical illustration of an image of an anatomically-aligned articulation as registered with indicia corresponding to the coordinate axes of FIG. 3.

Referring particularly to FIG. 4, the subject articulation is shown as an intervertebral joint of the spinal column wherein thoracic vertebrae T6–T16 and lumbar vertebrae L1–L5 are visible. Also visible within exposure 32a are the intervertebral discs, one of which is referenced at 60, the fibs, one of which is referenced at 62, and the pelvis, shown generally at 64 to include the bones of the ilium, 66, the ishium, 68, and the pubis, 70. For contrasting the image thereof, the film of exposure 32a is received, for example, within a radiograph reader, 80, which may have a backlighted surface, 82, and which allows for the translation of the film over the surface.

In accordance with the precepts of the present invention, surface 82 of reader 80 is provided with indicia lines, 90a, 90b, 90c, 90d, and 92, marked thereon. It will be appreciated that an orthogonal pair of line 92 and a line 90 will correspond to coordinate axes 40 (FIG. 3). Accordingly, the film of an exposure 32 may be aligned with an orthogonal pair of lines 90 and 92 to delineate the normal anatomical alignment of the articulation which, for spinal column 52, is represented by lines 90c and 92. It will be appreciated that additional indicia lines 90 and 92 may be provided to facilitate the alignment of exposure 32 therewith.

Figure 5:
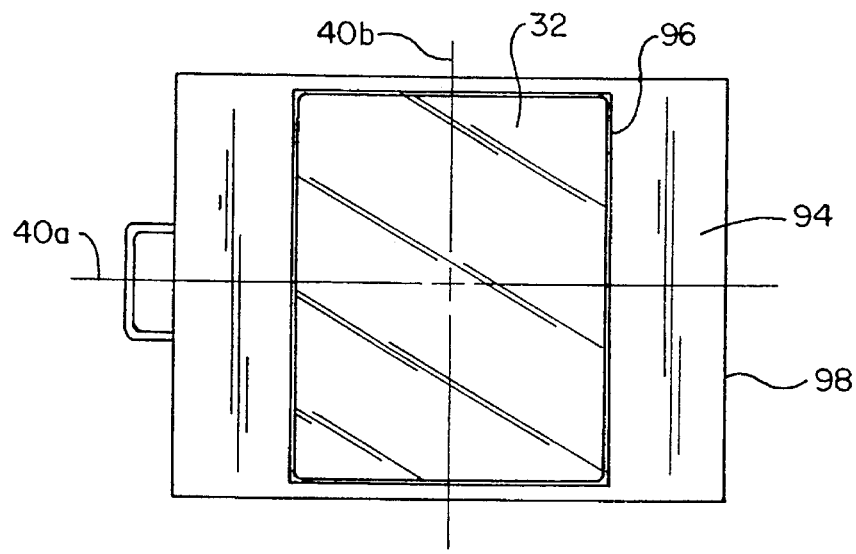
FIG. 5 is a stylized, graphical illustration of an image of a subluxed articulation as aligned with indicia corresponding to the coordinate axes of FIG. 3 for determining the degree of subluxation by the measurement of the deviation of the subluxed axis of the articulation from the indicia.

Looking additionally to FIG. 5, imagable surface 32 is shown as being received within a film holder, 94, which, in turn, is received by housing 34 (FIGS. 2 and 3). The generally polygonal periphery, 96, of surface 32 is aligned with the generally polygonal periphery, 98, of holder 94. As is shown, periphery 98 of holder 94, as received by housing 34, is in general alignment with coordinate axes 40. Such alignment thereby maintains periphery 96 of surface 32 in a corresponding alignment with axes 40. Accordingly, the alignment of periphery 96 of surface 32 with indicia lines 90 and 92 will be seen to dispose the image of the articulation with respect thereto in the same known position as the articulation was disposed with respect to coordinate axes 40.

Figure 6:
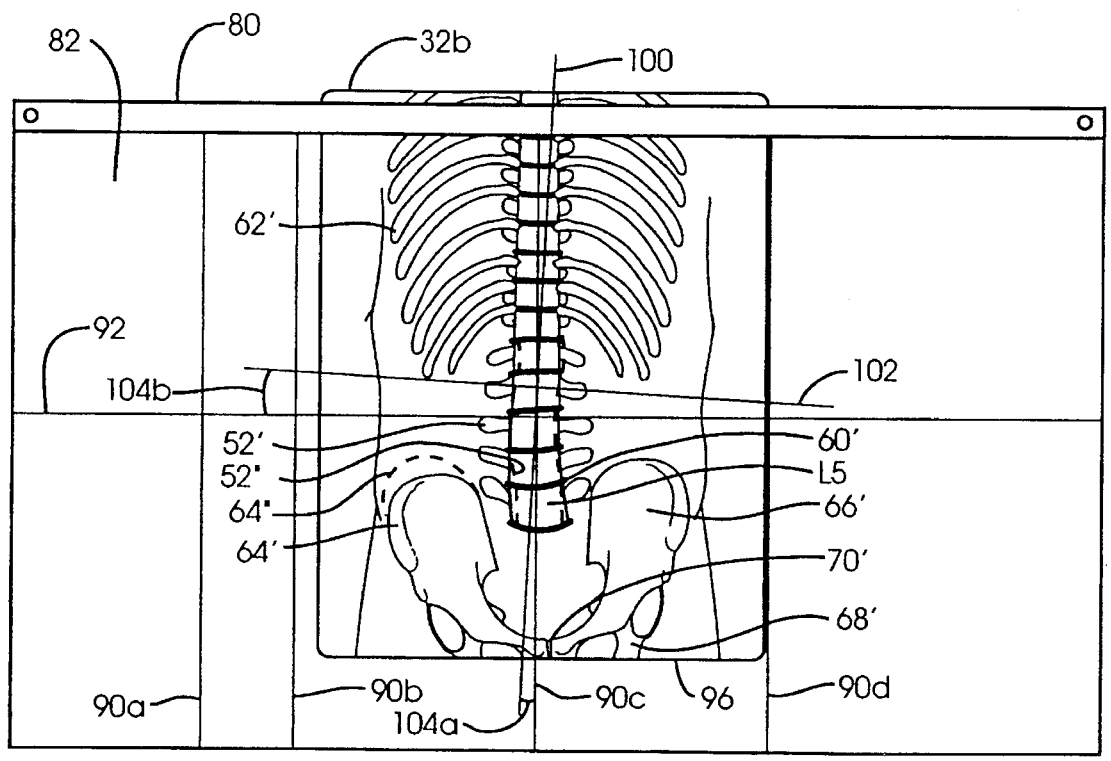
FIG. 6 is an anterior view of a patient presenting a pelvic obliquity as disposed in a known position with respect to the coordinate axes of FIG. 3 for the imaging of the subluxed axis of the obliquity.

Referring next to FIG. 6, spinal column 52' is presented as having a subluxation of the L5 vertebra, with disc 60, ribs 62, pelvis 64, ilium 66, ishium 68, and pubis 70 being presented, respectively, at 62', 64', 66', 68', and 70'. The film of exposure 32b is shown as being in alignment with lines 90c and 92, which lines correspond to the normal anatomic alignment of column 52', to dispose the image of the articulation in the same known position as the articulation was disposed with respect to coordinate axes 40 (FIGS. 2 and 3). With the subluxed axis of column 52' being given as represented by orthogonal lines 100 and 102, the degree of subluxation of column 52' from its normal anatomical alignment therefore may be determined, as is shown at 104a and 104b, by measuring the deviation of subluxed axis lines 100 and 102 from indicia lines 90c and 92.

Should a patient present a pelvic obliquity such as a scoliosis or other deformity caused by a shortened limb, for example, it is preferred that the obliquity is leveled prior to the imaging of the spinal column. Such an obliquity is represented in phantom in FIG. 6 at 52" and 64" as a displacement of pelvis 64 and a complex curvature of spinal column 52 making the subluxed articulation difficult to discern. With the obliquity leveled to place spine 52 and pelvis 64 generally in the positions represented at 52' and 64', the pathology of the scoliosis may be better diagnosed as caused, for example, by the subluxation of the L5 vertebra.

Figure 7:
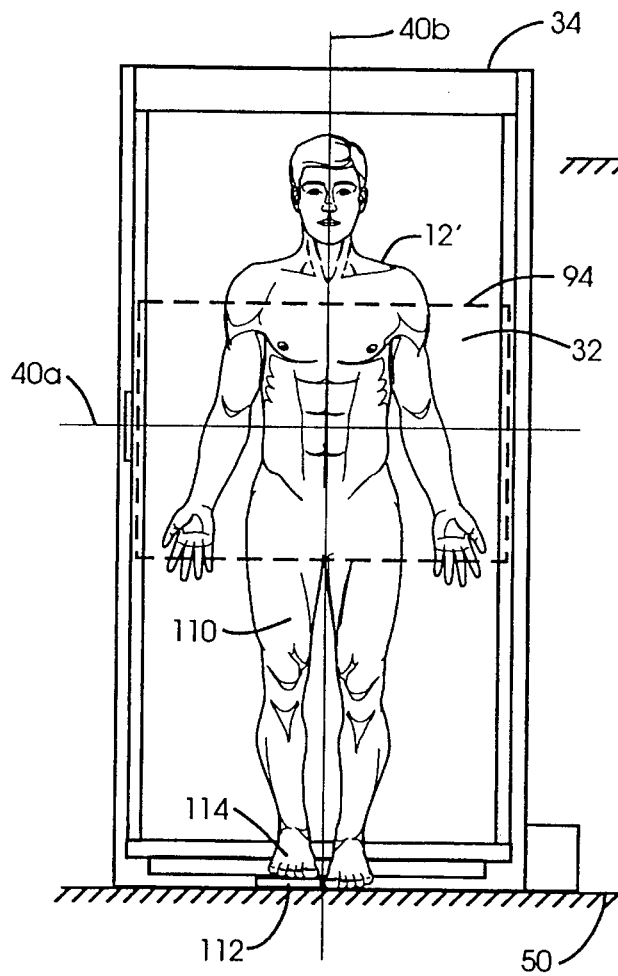
FIG. 7 is a plan view showing in enhanced detail the alignment of the imagable surface of FIG. 1 generally parallel to the coordinate axes of FIG. 3.

For an appreciation of the aforementioned leveling, reference is made to FIG. 7, wherein body 12 (FIGS. 2 and 3) is shown at 12' as presenting a pelvic obliquity caused by a shortening of a limb, such as leg 110, for example. To level the obliquity, a spacer member, 112, is interposed between foot 114 of leg 110 and support surface 50. Spacer member 112 is selected has having a thickness effective to dispose body 12' in a position wherein the spinal column and pelvis thereof are caused to be displaced into the positions represented at 52' and 64' of FIG. 6. Again, with the obliquity leveled, the pathology of the scoliosis or like deformity may be better diagnosed.

In view of the foregoing, a methodology has been described which provides for an objective determination of the degree of subluxation of an articulation such as an intervertebral or appendicular joint. Such methodology will be appreciated to assist the practitioner in rendering a more definitive pathogenic diagnosis of the physiological cause of the LBP, scoliosis, or like symptomology manifested in the articulation, or to confirm a diagnosis made on the basis of patient history and physical examination. It therefore is preferred that the methodology of the invention as described herein be practiced as part of a comprehensive management protocol for the diagnosing and treating of a patient experiencing pain in the range of motion of a subluxed articulation. Within such a protocol, the method may be used to assist the practitioner in localizing the physiological cause of the pain to a specific subluxed articulation. With the source of pain localized to a specific subluxed articulation, and the degree of subluxation of that articulation determined as previously described, a treatment program may be prescribed in accordance therewith.

Figure 8:
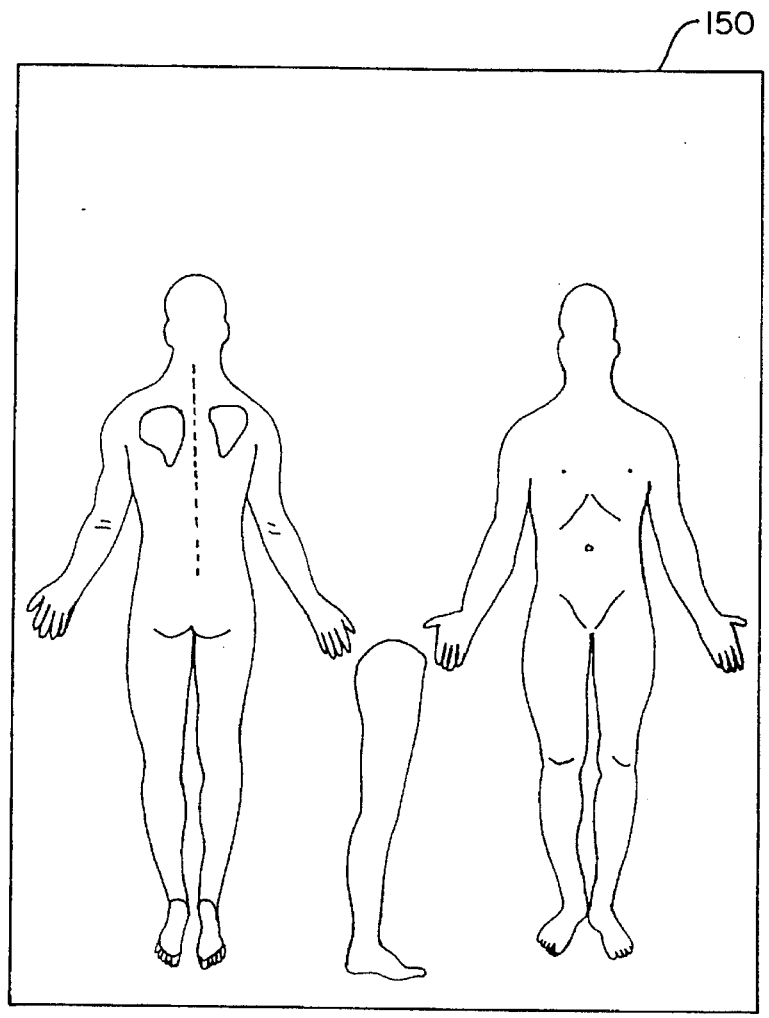
FIG. 8 is a representation of a pain diagram for use in conjunction with a comprehensive diagnosis and treatment protocol for the management of a patient experiencing pain in the range of motion of an articulation.

As part of the comprehensive management protocol, a pain diagram, a representation of which is shown in FIG. 8 at 150, is recommended for use in conjunction with a patient history and physical examination. For a patient exhibiting LBP symptomology or the like, the physical examination may involve flexion, extension, and lateral extension, i.e., side bend, movements of the back. Clinical observations during the exam should distinguish the symptoms, which may be plotted on diagram 150, of an acute or chronic pain pattern from those of distress or illness behavior. With the symptoms marked on the pain diagram, the patient may be asked to commit to a primary source of pain localized to a specific articulation, and to any secondary sources on the opposite side of the articulation. These sources then may be tracked over the course of treatment. The clinical diagnosis made on the basis of patient history and the physical examination may be confirmed and further assessed, in accordance with the methodology of the present invention, with an objective determination of the degree of subluxation of the articulation.

With the primary and any secondary sources of pain localized and confirmed, a nonoperative treatment modality may be prescribed which is specific to the primary source, and which is based on the degree of subluxation of the subluxed articulation at that source. Such treatments may include an epidural or facet injection of the affected joint area with an anti-inflammatory, corticosteroid such as dexamethasone (Decadron®) and/or with an analgesic such as lidocaine (Xylocaine®), in addition to an exercise regime tailored to increase the range of motion of the joint. As is shown in the exemplary clinical notes which follow, such a treatment modality has been observed to effect a more favorable prognosis than the generalized methods heretofore recommended in the literature.

The Examples to follow are illustrative of the practicing of the present invention, but should not be construed as limiting.

EXAMPLES

Example 1

The patient, a 32-year-old woman, presented painful dorsal and lumbar regions which were ultimately diagnosed as a scoliosis caused by a pelvic obliquity and an injury. The scoliosis exhibited both a rotational component in the T12-L1 area with a concavity of the fight dorsal and left lumbar spine, as well as an involvement of the cervical spine.

In examining the patient for scoliosis, the pelvic obliquity was leveled and the spine was imaged with standing radiographs. From the radiographs, it was determined that the scoliosis was not hereditary but began with the subluxation of a joint. Treatment involved the injection of the painful intervertebral joints with Xylocaine® and Decadron®. Decadron® was prescribed for its softening and anti-inflammatory properties to mobilize the joint capsule allowing the joint to resume a normal anatomic alignment. Once the pain had been managed, a voluntary exercise program was implemented which involved torso rotation to the left to release the right side concavity and lumbar extension. However, because of the degree of curvature in the lumbar region and the rotational component at T12-L1, a full extension of the lumbar spine and replacement of the mobilized joints to match the subluxed joints could not be achieved. Alternatively, the pelvis was mobilized with mechanical traction of the right side lumbar region. Radiographs subsequently showed a continuing improvement in the scoliosis without surgical intervention.

Example 2

A 32-year-old woman presented a scoliosis which was onset in her early twenties and which was exacerbation in her late twenties. The scoliosis exhibited the classic curvature of the cervical, dorsal, and lumbar spine with a rotational component to the right, primarily at T12-L1. It was determined that the scoliosis resulted from a ⅜-inch (9.5 mm) shorten right leg causing the lumbar curvature, and from injuries sustained during sports activity. Through the years, the gravitational forces on the lumbar spine caused the curvatures and the rotational component of the T12-L1 area.

Prior to treatment, the scoliosis was leveled at the sacral takeoff to align the vertebrae. From a standing radiograph examined with an indicia grid, it was evident that the lumbar spine followed the sacral takeoff, and then curved by a righting reflex for the patient to assume an erect posture. Upon an analysis of the angles of the scoliosis, it was determined that there had been the subluxation of an intervertebral joint, which was probably caused by injury.

The injection of Decadron® and Xylocaine® into the affected areas mobilized the subluxed joint by allowing a stretching the connective tissue which straightened the spine. An exercise program also was implemented to correct the subluxations. Over a period of one year, an acceptable 20° curvature in the T12-L1,2 area resulted with a complete, nonoperative straightening of the dorsal and cervical spine.

Example 3

A 45-year-old man presented a work-related injury which occurred one day prior to his examination. The injury occurred when the patient lifted from the left, causing a lift and twist. He did not use his legs and arms, but instead used his lower back to lift weight from the left side. A few hours after the injury, the patient was listing to the left. The next day, he experienced severe lumbar pain and was unable to straighten. On continuing history, the pain did not refer into the lower extremities.

Upon clinical examination, the patient was able to flex, mainly from the hips, but with some flexion of the lumbar spine. Extension was more to the left than right, but diminished overall. The lateral bend to the left was full, but was 0° to the right with severe pain accompanying. The patient was unable to tolerate the stress on the joint capsule at the L3-4 level on the right side, thus causing a severe sprain and dislocation of the intervertebral joint at that level. A pain diagram exhibited a pattern which was localized above the iliac crest on the right side of the pelvis.

Standing radiographs film showed a list from the right or subluxation on the left at the L3-4 intervertebral joint. Palpation of the lumbar spine in prone position showed that pain was localized to the L3-4 intervertebral joint.

The patient was treated with an injection of Decadron® and Xylocaine® to the intervertebral joint capsule on the right side at L3-4, and with ice massage and ultrasound. Prednisone was prescribed, and the exercise program was implemented which involved forward flexion and a bend to the right. Within three days, the patient has assumed an upright posture and was able to return to work with a full range of motion.

As it is anticipated that certain changes may be made in the present invention without departing from the precepts herein involved, it is intended that all matter contained in the foregoing description shall be interpreted as illustrative and not in a limiting sense.

What is claimed:

1. A method for managing a patient experiencing pain in the range of motion of an articulation having a skeletal structure normally in an anatomical alignment, where said articulation is an intervertebral joint of the spinal column, said method comprising the steps of:
    (a) diagnosing a subluxation of the articulation from its normal anatomical alignment by:
        (i) providing an imagable surface aligned generally parallel to a pair of coordinate axes, said coordinate axes corresponding to the normal anatomical alignment of the articulation;
        (ii) disposing the articulation in a known position with respect to said coordinate axes;
        (iii) imaging the articulation on said imagable surface to expose a subluxed axis thereof;
        (iv) aligning the image of the articulation with indicia corresponding to said coordinate axes to dispose said image in said known position with respect to said indicia; and
        (v) determining a degree of subluxation of the articulation from its normal anatomical alignment by measuring any deviation of the subluxed axis of the articulation from said indicia; and
    (b) treating the subluxation of the articulation based on the degree of subluxation determined in step (a)(v).

2. The method of claim 1 further comprising the step prior to step (a)(iii) of applying a physiologic load to the articulation.

3. The method of claim 1 wherein the articulation is radiographically imaged in step (a)(iii).

4. The method of claim 1 wherein the body of the patient is described by sagittal, coronal, and transverse reference planes, and wherein the articulation is disposed in a known position in step (a)(ii) by aligning the intersection of an orthogonal pair of the reference planes with said coordinate axes.

5. The method of claim 1 further comprising the step of:
    (a)(vi) assessing a disk of said intercerteb ral joint involved in causing the pain experienced by the patient.

6. The method of claim 1 further comprising the step of:
    (a)(vi) assessing a cause of the pain experienced by the patient.

7. The method of claim 1 wherein the body of the patient is described by a mid-sagittal and a transverse reference plane, and wherein the articulation is disposed in a known position in step (a)(ii) by aligning the intersection of the mid-sagittal and transverse reference planes with said coordinate axes.

8. The method of claim 1 further comprising the steps prior to step (a)(ii) of:

providing a support surface generally perpendicular to said imagable surface; and applying a physiologic load to the intervertebral joint by disposing the patient in a standing position on said support surface.

9. The method of claim 8 wherein the patient presents a pelvic obliquity and further comprising the step prior to step (a)(ii) of leveling the obliquity.

10. The method of claim 9 wherein the obliquity is leveled by interposing a spacer member between a foot of the patient and said support surface.

11. The method of claim 1 wherein the patient presents a scoliosis and further comprising the step of:

(a)(vi) assessing a cause of the scoliosis.

12. The method of claim 1 wherein the articulation is an appendicular joint.

13. A method for diagnosing in a human body a subluxation of an articulation from its normal anatomical alignment, where said articulation is an intervertebral joint of the spinal column, said method comprising the steps of:

(a) providing an imagable surface aligned generally parallel to a pair of coordinate axes, said coordinate axes corresponding to the normal anatomical alignment of the articulation;

(b) disposing the articulation in a known position with respect to said coordinate axes;

(c) imaging the articulation on said imagable surface to expose a subluxed axis thereof;

(d) aligning the image of the articulation with indicia corresponding to said coordinate axes to dispose said image in said known position with respect to said indicia; and (e) determining the degree of subluxation of the articulation from its normal anatomical alignment by measuring any deviation of the subluxed axis of the articulation from said indicia.

14. The method of claim 13 further comprising the step prior to step (c) of applying a physiologic load to the articulation.

15. The method of claim 13 wherein the articulation is radiographically imaged in step (c).

16. The method of claim 13 wherein the body is described by sagittal, coronal, and transverse reference planes, and wherein the articulation is disposed in a known position in step (b) by aligning the intersection of an orthogonal pair of the reference planes with said coordinate axes.

17. The method of claim 13 wherein the body is described by a mid-sagittal and a transverse reference plane, and, wherein the articulation is disposed in a known position in step (b) by aligning the intersection of the mid-sagittal and transverse reference planes with said coordinate axes.

18. The method of claim 13 further Comprising the steps prior to step (b) of:

providing a support surface generally perpendicular to said imagable surface; and applying a physiologic load to the intervertebral joint by disposing the body in a standing position on said support surface.

19. The method of claim 18 wherein the body presents a pelvic obliquity and further comprising the step prior to step (b) of leveling the obliquity.

20. The method of claim 19 wherein the obliquity is leveled by interposing a spacer member between a foot of the body and said support surface.

21. The method of claim 13 wherein the articulation is an appendicular joint.

* * * * *